(12) United States Patent
Conklin et al.

(10) Patent No.: US 6,383,761 B2
(45) Date of Patent: *May 7, 2002

(54) METHODS AND COMPOSITIONS FOR IDENTIFYING MODULATORS OF G-PROTEIN-COUPLED RECEPTORS

(75) Inventors: Bruce R. Conklin, San Francisco, CA (US); Evi Kostenis, Bethesda; Jürgen Wess, Rockville, both of MD (US)

(73) Assignees: The Regents of the University of California, Oakland, CA (US); National Institutes of Health, Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,345
(22) PCT Filed: Jul. 27, 1998
(86) PCT No.: PCT/US98/15567
§ 371 Date: Jul. 27, 1998
§ 102(e) Date: Jul. 27, 1998
(87) PCT Pub. No.: WO99/05177
PCT Pub. Date: Feb. 4, 1999

Related U.S. Application Data
(60) Provisional application No. 60/053,935, filed on Jul. 28, 1997.

(51) Int. Cl.[7] .................. G01N 33/567; C12N 15/12
(52) U.S. Cl. .................. 435/7.21; 435/7.1; 435/7.2; 435/69.1; 536/23.5
(58) Field of Search .................. 435/7.2, 7.1, 69.1, 435/69.7, 252.3, 320.1; 530/350; 536/23.6

(56) References Cited

PUBLICATIONS

Helper et al. Functional Importance of the Amino Terminus of Gq alpha. J. Biol. Chem. 271(1):496–504, Jan. 1996.*
Kostenis, E. et al., (Aug. 1, 1997) "The N–terminal extension of $G\alpha_q$ is critical for constraining the selectivity of receptor coupling" *The Journal of Biological Chemistry* 272(31):19107–19110.
Kostenis, E. et al., (Jul. 10, 1998) "Functional characterization of a series of mutant G protein $\alpha_q$ subunits displaying promiscuous receptor coupling properties" *The Journal of Biological Chemistry* 273(28):17886–17892.
Ashkenazi et al., "An M2 muscarinic receptor subtype coupled to both adenylyl cyclase and phosphoinositide turnover" *Science* 238(4827):672–675 (1987).
Berstein et al., "Reconstitution of agonist–stimulated phosphatidylinositol 4,5–bisphosphate hydrolysis using purified m1 muscarinic receptor, Gq/11, and phospholipase C–beta 1" *J. Biol. Chem.* 267(12):8081–8088 (1992).
Bonner et al., "Identification of a family of muscarinic acetylcholine receptor genes" *Science* 237(4814):527–532 (1987).
Boss et al., "Induction of NFAT–mediated transcription by Gq–coupled receptors in lymphoid and non–lymphoid cells" *J. Biol. Chem.* 271(18):10429–10432 (1996).
Camps et al., "Isozyme–selective stimulation of phospholipase C–beta 2 by G protein beta gamma–subunits" *Nature* 360(6405):684–686 (1992).
Conklin et al., "Substitution of three amino acids switches receptor specificity of Gq alpha to that of Gi alpha" *Nature* 363(6426):274–276 (1993).
Conklin et al., "Carboxyl–terminal mutations of Gq alpha and Gs alpha that alter the fidelity of receptor activation" *Mol. Pharmacol.* 50(4):885–890 (1996).
Cullen, "Use of eukaryotic expression technology in the functional analysis of cloned genes" *Meth. Enzymol.* 152:684–704 (1987).
Degtyarev et al., "Palmitoylation of a G protein alpha I subunit requires membrane localization not myristoylation" *J. Biol. Chem.* 269:30898–30903 (1994).
Edgerton et al., "Palmitoylation but not the extreme am9ino–terminus of Gq alpha is required for coupling to the NK2 receptor" *FEBS Letter* 354:195–199 (1994).
Gocayne et al., "Primary structure of rat cardiac beta–adrenergic and muscarinic cholinergic receptors obtained by automated DNA sequence analysis: Further evidence for a multigene family" *PNAS USA* 84(23):8296–8300 (1987).
Gomeza et al., "Coupling of metabotropic glutamate receptors 2 and 4 to $G_{\alpha15}$, $G_{\alpha16}$, and chimeric $G_{\alpha q/I}$ proteins: Characterization of new antagonists" *Mol. Pharmacol.* 50:923–930 (1996).
Grandy et al., "Cloning of the cDNA and gene for a human D2 dopamine receptor " *PNAS USA* 86(24):9762–9766 (1989).
Helper et al., "Functional importance of the amino terminus of Gq alpha" *J. Biol. Chem.* 271(1):496–504 (1996).
Kalinec et al., "Mutated α subunit of the $G_q$ protein induces malignant transformation in NIH 3T3 cells" *Mol. & Cell. Biol.* 12(10):4687–4693 (1992).
Katz et al., "Subunits beta gamma of heterotrimeric G protein activate beta 2 isoform of phospholipase C" *Nature* 360(6405):686–689 (1992).
Kostenis et al., "Molecular basis of receptor/G protein coupling selectivity studied coexpression of wild type and mutant m2 muscarinic receptors with mutant Galpha(q) subunits" *Biochem.* 36:1487–1495 (1997).
Liu et al., "Identification of a receptor/G–protein contact site critical for signaling specificity and G–protein activation" *PNAS USA* 92(25):11642–11646 (1995).

(List continued on next page.)

*Primary Examiner*—John Ulm
(74) *Attorney, Agent, or Firm*—Morrison & Foerster LLP

(57) ABSTRACT

The present invention provides methods and compositions that can be used to identify modulators of G-protein-coupled receptors.

78 Claims, 6 Drawing Sheets

OTHER PUBLICATIONS

Mahan et al., "Cloning and expression of an A1 adenosine receptor from rat brain" *Mol. Pharmacol.* *40*(1):1–7 (1991).

McCallum et al., "The role of palmitoylation of the guanine nucleotide binding protein G11 alpha in defining interaction with the plasma membrane" *Biochem. J.* *310*(Pt 3):1021–1027 (1995).

Neer, "Heterotrimeric G proteins: Organizers of transmembrane signals" *Cell* *80*(2):249–257 (1995).

Offermanns et al., "Transfected muscarinic acetycholinereceptors selectively couple to Gi–type G proteins and Gq/11" *Mol. Pharmacol.* *45*(5):890–898 (1994).

Sanger et al., "DNA sequencing with chain–terminating inhibitors" *PNAS USA* *74*(12):5463–5467 (1977).

Schöneberg et al., "Functional rescue of mutant V2 vasopressin receptors causing nephrogenic diabetes insipidus by a co–expressed receptor polypeptide" *EMBO J.* *15*(6):1283–1291 (1996).

Smrcka et al.,"Regulation of polyphosphoinositide–specific phopholipase C activity by purified Gq." *Science* *251*(4995):804–807 (1991).

Strathmann et al.,"G protein diversity: A distinct class of alpha subunits is present vertebrates and invertebrates" *PNAS USA* *87*(23):9113–9117 (1990).

Watson et al., *The G–Protein Linked Receptor–Facts Book*-(Watson, S., and Arkinstall, S., eds., Academic Press, London), pp. 1–291 (1994).

Wedegaertner et al., "Palmitoylation is required for signaling functions and membrane attachment of Gq alpha and Gs alpha" *J. Biol. Chem.* *268*(33):25001–25008 (1993).

Yamada et al., "Cloning and functional characterization of a family of human and mouse somatostatin receptors expressed in brain, gastrointestinal tract, anf kidney" *PNAS USA* *89*(1):251–255 (1992).

Zhou et al., "Cloning and expression of human and rat D1 dopamine receptors" *Nature* *347*(6288):76–80 (1990).

Zhu et al., "Cloning of a human kappa opioid receptor from the brain" *Life Sci.* *56*(9):201–207 (1995).

\* cited by examiner

FIGURE 1

```
                                      αN Helix
                  1      7 9 10  ─────────────
αq (WTq)  MTLESIMAC.CLS......EEAK  -
 -6q              MAC.CLS......EEAK  -
α11       MTLESMMAC.CLS......DEVK  -

αi1,3            MGC.TLS......AEDK  -
αo1,2            MGC.TLS......AEER  -
αt1              MGA.GAS......AEEK  -

αs              MGCLGNSKTEDQRNEEK  -
```

The G$_\alpha$ protein Family Tree

METHODS AND COMPOSITIONS FOR IDENTIFYING MODULATORS OF G-PROTEIN-COUPLED RECEPTORS

CROSS-REFERENCE TO RELATED APPLICATIONS

This application is the U.S. National Phase of international application PCT/US98/15567 filed Jul. 27, 1998, which claims priority to U.S. provisional application No. 60/053,935, which was filed Jul. 28, 1997.

This invention was made with Government support under Grant No. HL02555, awarded by the National Institutes of Health. The Government has certain rights in this invention.

TECHNICAL FIELD

This invention relates to signal transduction via G-protein-coupled receptors (hereinafter GPCRs).

More specifically, this invention relates to compositions and methods for screening modulators of GPCRs. The compositions and methods involve mutated G proteins that can be used to shift signal transduction of certain classes of GPCRs to an alternative effector pathway that can be measured by high throughput screening techniques. Generation of such mutants therefore facilitates large-scale rapid screening for candidate GPCR modulators having diagnostic and/or therapeutic benefit.

BACKGROUND OF THE INVENTION

The interaction between extracellular ligands and cell surface receptors is of central importance in the sensitivity and responsiveness of eukaryotic cells to exogenous signals and other environmental stimuli. Over the past decades, numerous cell surface receptors have been discovered, characterized and cloned. Among them, G-protein-coupled receptors (GPCRS) plays a pivotal role in a wide range of physiological responses.

G-protein-coupled receptors form a large family of related proteins. Members of each subfamily are coupled to different subsets of downstream signal transduction components that transduce and amplify distinct arrays of intracellular signals. In particular, GPCRs generally comprise a characteristic group of seven transmembrane spanning regions, and are further characterized by their ability to interact with heteromultimeric G-protein complexes, which are generally trimeric complexes comprised of $\alpha$, $\beta$ and $\gamma$ subunits. Typically, activation of a GPCR by an agonist (i.e. a positive modulator such as a specific ligand) causes the GPCR to interact with and activate a particular class of G protein. In the activated G protein, GDP bound to the a subunit is replaced with GTP followed by the dissociation of $\alpha_{GTP}$ from the $\beta\gamma$ dimer. The activated G protein subunits ($\alpha_{GTP}$ or free $\beta\gamma$) are then able to modulate downstream signal transduction events via one or more "effector" molecules (typically via effector enzymes and/or the modulation of ion channels. Many effectors can be regulated by the $\alpha$ subunit and independently co-regulated (either positively or negatively) by the $\beta\gamma$ units (see, e.g., E. J. Neer, Cell 80: 249–257, 1995).

At least four subfamilies of G protein $\alpha$ subunits have been identified to date, namely $\alpha_q$, $\alpha_s$, $\alpha_i$ and $\alpha_{12}$ (as illustrated in FIG. 6), and multiple $\beta$ and $\gamma$ subunits have been found. More than half of GPCRs appear to couple to the heterotrimeric G proteins Gs or Gi in which the $\alpha$ subunit is $\alpha_s$ or $\alpha_i$. Both Gs and Gi signal through the cyclic AMP (cAMP) pathway. In particular, Gs stimulates adenylyl cyclase, resulting in an increase in intracellular cAMP concentration, whereas Gi inhibits adenylyl cyclase, causing a decrease in intracellular cAMP level. A smaller number of GPCRs activate a phospholipase C (PLC) pathway by coupling with a distinct group of heterotrimeric G proteins, Gq in which the $\alpha$ subunit is $\alpha_q$. Phospholipase C hydrolyzes phosphoinositides to generate two classes of well-characterized second messengers, namely, diacylglycerol and inositol phosphates. Diacylglycerol activates certain protein kinase Cs (PKCs) and certain inositol phosphates stimulate the mobilization of calcium from intracellular stores.

Among the physiological responses involving signal transduction via GPCRs are the dilation/constriction of blood vessels, bronchi and organs within the gastrointestinal tract, the modulation of endocrine secretions, and the control of heart rate. Indeed, in mammals it is believed that more than 1000 genes encode GPCRs of one type or another. Of those, several hundred GPCRs are likely to be involved in various disease processes, and thus are potential diagnostic and/or therapeutic targets. While GPCR modulators (including agonists and antagonists for example) have a great potential as diagnostic/therapeutic agents, the search for such agents is often both time consuming and labor intensive.

While some screening assays have been described, many assays are either inconvenient to perform on a large scale, or their uses are limited to only a subset of GPCRs. For example, while calcium mobilization (a downstream event associated with Gq activation) is amenable to high throughput screening using robotic assays, the majority of GPCRs are not coupled to Gq. Conversely, while many GPCRs are coupled to G proteins affecting changes in cyclic AMP (i.e. Gs or Gi as noted above), changes in cAMP level are not particularly amenable to high throughput or robotic screening assays.

There thus remains a considerable need for compositions and methods that can be used to facilitate the large-scale and rapid screening of GPCR modulatory agents, particularly agents that modulate GPCRs that are associated with alterations in intracellular cAMP (which collectively represent the majority of known GPCRs).

SUMMARY OF THE INVENTION

The present invention provides compositions and methods for identifying agents that modulate G-protein-coupled receptors, particularly agents that modulate non-Gq-coupled receptors (such as Gi- or Gs-coupled receptors), using high throughput screening methods based on Gq signaling.

In essence, the compositions and methods of the present invention effectively couple non-q upstream signaling events (such as those initiated by ligand binding to Gi- or Gs-coupled receptors) to q-type downstream signaling, such as calcium mobilization, that is readily amenable to high throughput screening techniques. The effective shift in signal transduction pathways greatly facilitates screening for GPCR modulatory compounds which would be of major diagnostic and therapeutic potential.

BRIEF DESCRIPTION OF THE DRAWINGS

FIG. 1 depicts the comparison of the N-terminal amino acid sequences of selected G protein $\alpha$ subunits. Gaps were introduced to allow for maximum sequence identity. The position of the N-terminal portion of the $\alpha$N helix, as revealed by X-ray crystallography is indicated. "-6q" denotes a mutant $G\alpha_q$ construct lacking the first six amino acids.

DETAILED DESCRIPTION OF THE INVENTION

Figure 2A:
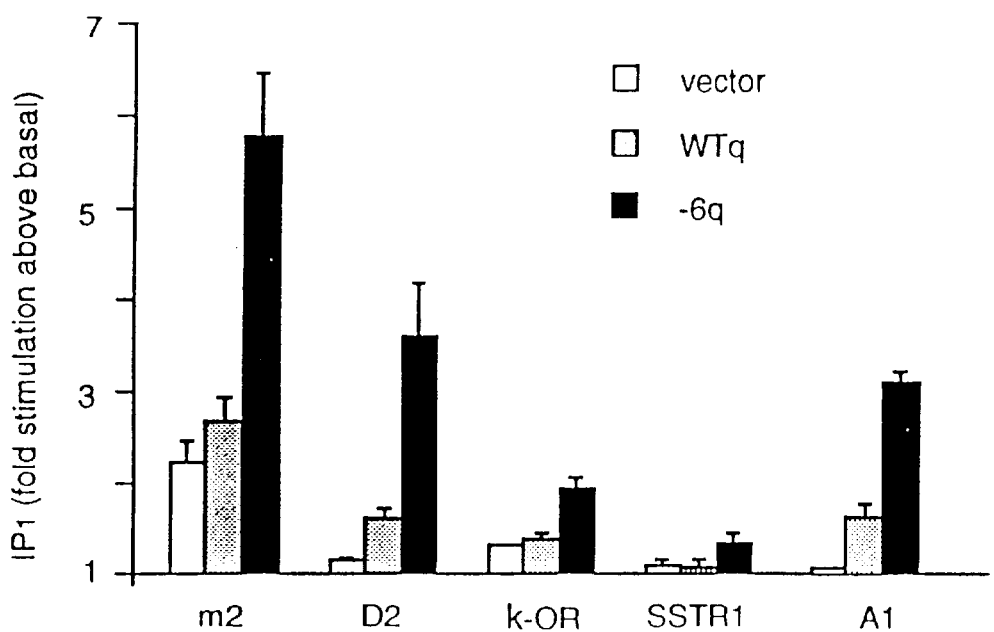
FIG. 2 depicts the functional interaction of different G protein-coupled receptors with the Gα subunits, WTq and −6q. COS-7 cells co-expressing WTq or −6q and different Gi/o-coupled receptors (A) or Gs-coupled receptors (B) were incubated for 1 h (at 37° C.) in the absence or presence of the indicated agonist ligands. The resulting increases in intracellular $IP_1$ levels were determined as described under "Example 3". Data are given as means ±S.E. of three to seven independent experiments, each carried out in triplicate. The following receptors: ligands were used: (A) m2 muscarinic receptor: carbachol (100 μM); D2 dopamine receptor: (−)-quinpirole (10 μM); κ-opioid receptor (κ-OR): (−)-U50488 (10 μM); somatostatin SSTR1 receptor: somatostatin-14 (1 μM); (B) A1 adenosine receptor: (−)-PIA (R(−)-$N^6$-(2-Phenylisopropyl)-adenosine (10 μM); D1 dopamine receptor: dopamine (1 mM); V2 vasopressin receptor: [$Arg^8$]vasopressin (1 nM); β2-adrenergic receptor: (−)-isoproterenol (200 μM).

As noted above, the present invention provides compositions and methods for identifying agents that modulate G-protein-coupled receptors, particularly agents that modulate non-Gq-coupled receptors (such as Gi- or Gs-coupled receptors), using high throughput screening methods based on downstream events normally associated with Gq signaling. The compositions and methods of the present invention effectively couple non-q upstream signaling events (such as those initiated by ligand binding to Gi- or Gs-coupled receptors) to q-type downstream signaling, such as calcium mobilization, that is readily amenable to high throughput screening techniques. The effective shift in signal transduction pathways greatly facilitates screening for GPCR modulatory compounds which would be of major diagnostic and therapeutic potential.

This invention encompasses nucleic acids encoding G protein $α_q$ mutants, cell lines expressing such mutants, and methods of using such mutants for the screening of GPCR modulators, particular modulators of Gi- and Gs-coupled GPCRs. The uses described include methods of high throughput screen of compounds that bind to or modulate the activities of non-Gq-coupled (such as Gi- and Gs-coupled GPCRs which collectively constitute the majority of known GPCRs). The invention also includes compounds for modulating these receptors identified by such methods of screening.

DEFINITIONS

The terms "polypeptide", "peptide" and "protein" are used interchangeably to refer to polymers of amino acids and do not refer to any particular lengths of the polymers. Also included within the definition are, for example, proteins containing one or more analogs of an amino acid (including, for example, unnatural amino acids, etc.), proteins with substituted linkages, as well as other modifications known in the art, both naturally occurring and non-naturally occurring. It is also known in the art that many proteins are post-translationally modified in eukyotic cells in a number of ways, including but not limited to glycosylation, acetylation, phosphorylation, myristoylation, and palmitoylation. For instance, many G proteins described herein, for example, $Gα_q$, $Gα_s$ and $Gα_i$ are either palmitoylated or myristoylated.

"Domain" refers to a portion of a protein or peptide that is physically or functionally distinguished from other portions of the protein or peptide. Physically-defined domains include those amino acid sequences that are exceptionally hydrophobic or hydrophilic, such as those sequences that are membrane-associated or cytoplasm-associated. Domains may also be defined by internal homologies that arise, for example, from gene duplication. Functionally-defined domains have a distinct biological function(s). The ligand-binding domain of a receptor, for example, is that domain that binds ligand. Functionally-defined domains need not be encoded by contiguous amino acid sequences. Functionally-defined domains may contain one or more physically-defined domain. Receptors, for example, are generally divided into the extracellular ligand-binding domain, a transmembrane domain, and an intracellular effector domain.

As used herein, a "polynucleotide" or "nucleic acid" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double-stranded, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form. Not all linkages in a polynucleotide need be identical. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs.

A polynucleotide or polynucleotide region has a certain percentage (for example, 80%, 85%, 90%, or 95%) of "sequence identity" to another sequence means that, when aligned, that percentage of bases are the same in comparing the two sequences.

A nucleotide is said to "encode" a polypeptide if, in its native state or when manipulated by methods known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

An "open reading frame" (or "ORF") is a region of a polynucleotide sequence that can encode a polypeptide or a portion of a polypeptide (i.e., the region may represent a portion of a protein coding sequence or an entire protein coding sequence).

"Fused" or "fusion" refers to the joining together of two or more elements, components, etc., by whatever means (including, for example, a "fusion protein" made by chemical conjugation (whether covalent or non-covalent), as well as the use of an in-frame fusion to generate a "fusion protein" by recombinant means, as discussed infra). An "in-frame fusion" refers to the joining of two or more open reading frames (ORFs), by recombinant means, to form a single larger ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature). Although the reading frame is thus made continuous throughout the fused segments, the segments may be physically separated by, for example, in-frame flexible polypeptide linker sequences.

A "transcriptional regulatory region" or "transcriptional control region" refers to a polynucleotide encompassing all of the cis-acting sequences necessary for transcription, and may include sequences necessary for regulation. Thus, a transcriptional regulatory region includes at least a promoter sequence, and may also include other regulatory sequences such as enhancers, transcription factor binding sites, polyadenylation signals and splicing signals.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

"Mutant" forms of a protein or polypeptide are those which have alterations in amino acid sequence and/or structure caused, for example, by site-directed mutagenesis (on the nucleotide level) or other chemical modification (on the peptide level); by errors in transcription or translation; or which are prepared synthetically by rational design. Minor alterations are those which result in amino acid sequences wherein the biological activity of the polypeptide is retained and/or wherein the mutant polypeptide has at least 90% homology with the native form. As used herein, the biological activity of a mutant G protein is fundamentally defined by its ability to interact with GPCRs and with downstream targets. For example, certain mutant G proteins as described herein are functionally "promiscuous" with respect to upstream signaling (i.e. they have acquired the ability to be activated by GPCRs other than those to which the "parental-type" protein is normally coupled) while retaining their specificity with respect to downstream signaling (i.e. the retain the ability to activate the same set or sets of downstream effectors as the parental-type protein). As described herein, an exemplary group of such mutant G proteins has one or more alterations affecting the N-terminus of the $\alpha_q$ subunit which allows the G protein to interact with (and be activated by) Gi- and Gs-coupled GPCRs, but to convey the downstream signal that is normally associated with Gq signaling.

"Recombinant," as applied to a polynucleotide, means that the polynucleotide is the product of various combinations of cloning, restriction and/or ligation steps resulting in a construct that is distinct from a polynucleotide found in nature. Recombinant may also be used to refer to the protein product of a recombinant polynucleotide. By way of illustration, a nucleic acid sequences encoding a GPCR or a G protein subunit (such as a Gα subunit), can be assembled from cDNA fragments and short oligonucleotide linkers, or from a series of oligonucleotides, to provide a synthetic gene which is capable of being expressed when operably linked to a transcriptional regulatory region. The coding sequences are preferably provided in the form of an open reading frame uninterrupted by internal non-translated sequences (i.e. "introns"), such as those commonly found in eukaryotic genes. These and other nucleic acid sequences referred to in the context of the present invention can also be generally obtained by PCR amplification using viral, prokaryotic or eukaryotic DNA or RNA templates in conjunction with appropriate PCR amplimers.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

"Signal transduction" refers to a series of intercellular and subcellular events by which a chemical or physical signal is transmitted to a cell and is conveyed to a subcellular component or components that are involved in a response to the signal. Signal transduction mediated by G proteins can be conveniently divided into two stages in the context of the present invention. In particular, the G protein can be regarded as playing a pivotal role between: (i) "upstream" signal transduction events (including, for example, binding of a "first messenger" such as a ligand or agonist to a GPCR and consequent activation of a coupled G protein), and (ii) "downstream" signal transduction events (including, for example, the interaction of the activated G protein and/or G protein subunits with "effectors" such as ion channels or enzymes involved in the synthesis of "second messengers" like cyclic AMP or inositol phosphate).

A "G-protein-coupled receptor" or "GPCR" refers to a member of a class of cellular proteins involved in the receipt of an extracellular signal and the transmission of that signal to a G protein to which they are coupled. GPCRs can be organized into families based on structural and functional relatedness. As discussed herein, GPCRs can be grouped into families which collectively transduce a variety of different upstream signals (e.g. a variety of different chemical or physical signals) into a downstream pathway that is mediated by a particular class of G protein. For example, a large variety of GPCRs are coupled to G proteins of the Gi or Gs type, which effectively convey extracellular signals to effectors resulting in the inhibition or stimulation, respectively, of intracellular cyclic AMP.

Figure 6:
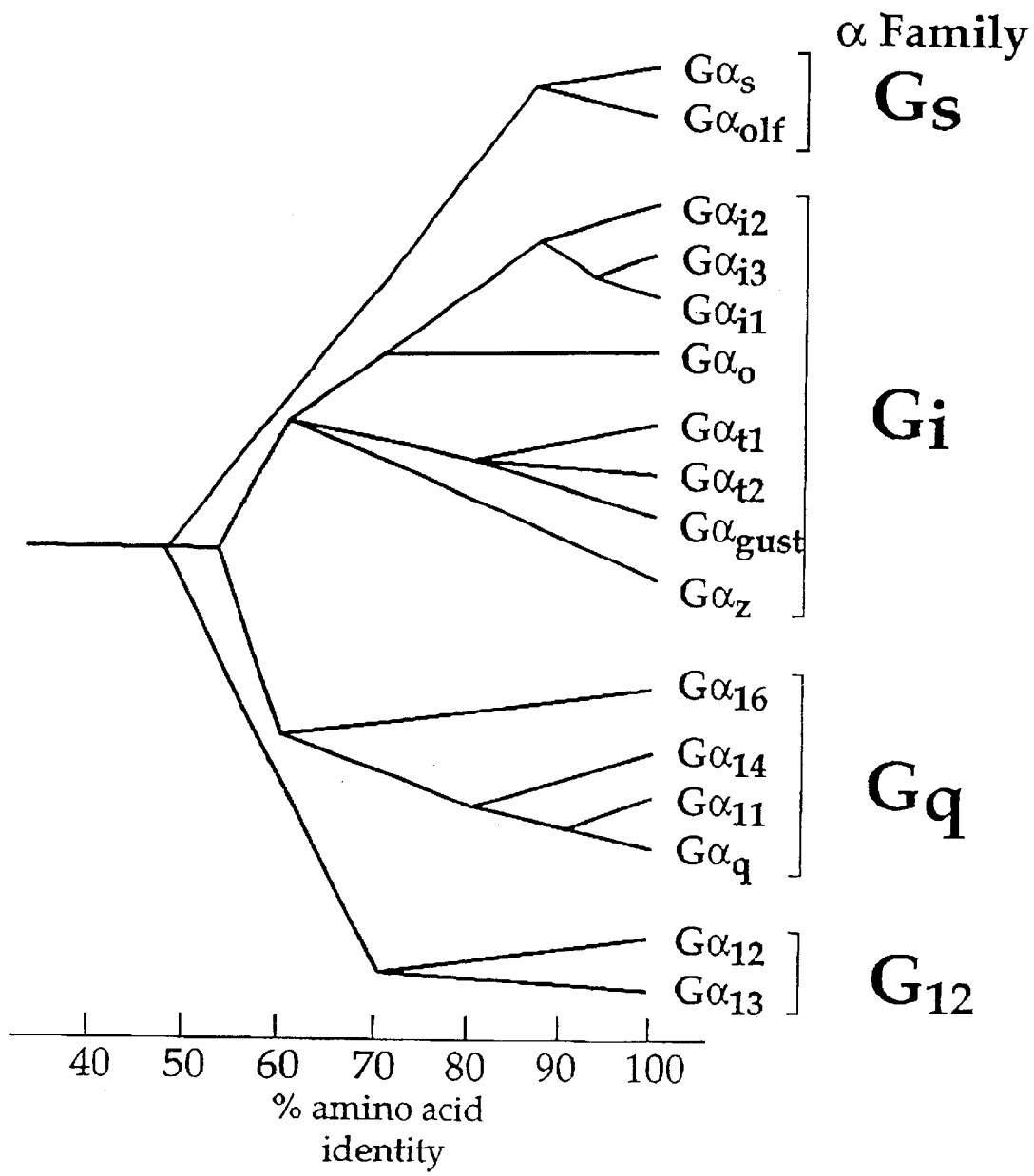
FIG. 6 illustrates the relationship of various G protein families and also shows the relative percent amino acid identity shared by various G protein families and individual types.

A "G protein" refers to a member of a class of cellular proteins that bind to GTP/GDP and which regulate the activity of a wide variety of cellular enzymes and/or ion channels. Many G proteins interact with GPCRs and effectively transduce a signal from the GPCR to downstream effectors. Such GPCR-interactive G proteins are typically heterotrimeric proteins (comprising α, β and γ subunits) that are activated by GPCRs having a characteristic group of seven transmembrane spanning regions. However, despite these commonalties, the G proteins differ in the nature of the GPCRs and effectors that they interact with or "talk" to, the specificity of which interaction appears to be essentially dependent on the nature of the G protein α subunit. For example, G proteins of the Gs type (which have an $\alpha_s$ subunit) are coupled to and activated by a class of GPCRs and, upon activation, mediate signal transduction to effectors that stimulate the production of cyclic AMP within the cell (typically as a result of dissociation of the activated G protein into α-GTP and a βγ dimer, as described above). Whereas G proteins of the Gi type (which have an $\alpha_i$ subunit) associate with another class of GPCRs to mediate inhibition of adenylyl cyclase, resulting in a decrease in cyclic AMP level. G proteins of the third class, namely the Gq type (which have an α subunit selected from a group of $\alpha_{16}, \alpha_{14}, \alpha_{11}, \alpha_q$ (see FIG. 6)) are coupled to another distinct class of GPCRs and, upon stimulation, mediate signaling via PLC-pathway.

A "promiscuous" G protein refers to a G protein that has acquired the ability to interact with receptors and/or effectors other than those with which it normally interacts; a phenomenon sometimes referred to as "cross-talk." By way of illustration, a promiscous Gq protein may exhibit the ability to interact with non-q-type receptors (such as Gi-type or Gs-type GPCRs, as described below).

An "effector," as used herein, refers to an intracellular protein or complex of proteins that mediate cellular responses to a signal such as that tranduced by GPCRs and their coupled G proteins. Effectors of G protein and/or G protein subunits may include adenylyl cyclases, phospholipase C enzymes, and phospholipase A2 enzymes (and other enzymes involved in the synthesis of second messengers), as well as ion channels that can be opened or closed as a result of activation of GPCRs and their associated G proteins.

As used herein, a receptor is considered to be "biologically active" if it is capable of binding ligand, and transmitting an intracellular signal or response. "Intracellular signal" and "intracellular response" are used interchangeably herein. The intracellular responses characteristic Gq-coupled receptor include coupling with $G\alpha_q$ subunit, a subsequent activation of phospholipase pathway.

A "modulator" refers to a compound which modulates a receptor, including agonists, antagonists, allosteric modulators, and the like. Typically, the modulator binds to the receptor (i.e. it acts as a ligand for the GPCR). GPCR modulators thus refer to agents that modulate (e.g. stimulate or inhibit) the activity of G-protein-coupled receptors. As is known in the art, inhibitors can bind reversibly (in which case they can usally be "competed off" by increasing the levels of the normal agonist), or they can bind irreversibly (in which case the inhibitory effect is observed to be non-competitive).

A "ligand" refers to a molecule capable of being bound by the ligand-binding domain of a receptor. The molecule may be chemically synthesized or may occur in nature. "Agonist" refers to a ligand capable of stimulating the biological activity of a receptor. "Antagonist" refers to a ligand capable of inhibiting the biological activity of a receptor.

Altered G Proteins that Engage in Promiscuous Signaling

Experiments carried out on several distinct classes of heterotrimeric G proteins have suggested the general principle that G-protein coupling specificity is determined primarily by the α subunit of the G protein.

The majority of known GPCRs influence the levels of cyclic AMP as a "second messenger" within the responding cell, and fall into one of two general classes depending on the nature of their α subunit and the consequent effector activity (i.e. either stimulation or inhibition of cyclic AMP). In particular, G proteins of the Gs type (which have an $\alpha_s$ subunit) are coupled to and activated by a class of GPCRs and, upon activation, mediate signal transduction to effectors that stimulate the production of cyclic AMP within the cell (typically as a result of dissociation of the activated G protein into α-GTP and a βγ dimer, as described above and in the art). Conversely, G proteins of the Gi type (which have an $\alpha_i$ subunit) are coupled to and activated by a class of GPCRs and, upon activation, mediate signal transduction to effectors that inhibit the production of cyclic AMP within the cell.

Another class of G proteins, of the Gq type (which have an $\alpha_q$ subunit), activate a phospholipase C (PLC) pathway, resulting in the hydrolysis of phosphoinositides to generate two classes of different second messengers, namely, diacylglycerol and inositol phosphates. Diacylglycerol activates certain protein kinase Cs (PKCs) and certain inositol phosphates stimulate the mobilization of calcium from intracellular stores.

Previously-described mutants capable of switching signaling from a non-q pathway to a q pathway comprised C-terminal alterations that appeared to switch signaling specificity from Gi to Gq (see B. R. Conklin et al., Nature 363: 274–276, 1993). More recently, C-terminal alterations that appeared to switch signaling specificity from Gs to Gq were described (see B. R. Conklin et al., Molecular Pharmacology 50: 885–890, 1996).

Published reports describing N-terminal alterations of $Gq_\alpha$ indicated that while the first six amino acids could be deleted without destroying the ability of the Gq to transduce its normal signal, alterations that impacted the cysteine residues (at positions 9 and 10) tended to disrupt both receptor and effector interaction (see, e.g., P. B. Wedegaertner, J. Biol. Chem., 268: 25001–25005, 1993; J. R. Hepler et al., J. Biol. Chem., 271: 496–504, 1996; and M. D. Edgerton et al., FEBS Letters 354: 195–199, 1994).

We have made the surprising discovery that N-terminal alterations of $Gq_\alpha$ subunits can be used to render Gq relatively promiscuous with respect to upstream signaling events in that such Gq proteins incorporating N-terminally altered $Gq_\alpha$ subunits acquire the ability to be activated by one or more non-Gq receptors, and yet still retain the downstream signaling capacity that is characteristic of the Gq receptor. Such N-terminal alterations in $Gq_\alpha$ can also be combined with C-terminal alterations to further modulate the ability of the mutant G proteins to engage in "cross-talk" with non-q GPCRs as a means of shunting non-q signaling to q-type effector events (such as calcium mobilization) that are amenable to high throughput screening.

The present invention provides compositions and methods by which non-q upstream signaling events (such as those arising from the activation of Gs-type or Gi-type GPCRs) are "shunted" to q-type downstream signaling events (such as the mobilization of intracellular calcium). Among other things, such compositions and methods allow for the screening of non-q modulators (such as a ligands or agonists capable of activating Gs-type or Gi-type GPCRS) using rapid and efficient high throughput screening methods that can be applied to the detection of downstream events such as calcium mobilization.

One embodiment of this invention provides recombinant nucleic acids encoding N-terminally altered $\alpha_q$ subunits, which render the altered Gq protein relatively promiscuous in that it acquires the ability to interact with one or more non-Gq-coupled receptors (such as Gs-type or Gi-type GPCRs). Whereas these promiscuous Gq mutants result in the ability to associate with one or more non-Gq receptors, they still retain the downstream signaling capacity that is characteristic of the Gq receptors (e.g. the ability to transmit signals from an activated receptor to downstream effectors such as PLCs, resulting in an augmentation of inositol phosphate levels and subsequent calcium mobilization). As a result, such altered G protein subunits (and the heterotrimeric G proteins into which they are incorporated) can be used to shunt non-Gq signaling (which is somewhat difficult to measure in a high throughput screening context) into Gq-type downstream signaling that can be readily measured using techniques that are amenable to high throughput assays and robotic screens.

Preferred examples of such altered $\alpha_q$ subunits comprise one or more alterations affecting the amino terminus, preferably a deletion, substitution and/or insertion that affects one or more of the first 10 amino acids, more preferably affecting one or more the first six amino acids, most preferably a mutation that deletes or disrupts the first six amino acids. As described below, we have shown that such N-terminally altered αq subunits can be used to allow Gq to associate with, and transduce the signal of, other GPCRs (such as Gi-type and Gs-type GPCRs).

Additional alterations can be introduced at the N-terminal region and/or the C-terminal region to further influence the signal transduction and/or to modulate the localization, activity or stability of the G protein. By way of illustration, we describe mutants below in which the first 6 amino acids have been removed, and adjacent amino acids have been switched (from q-type to non-q-type). We also describe mutants in which N-terminal alterations have been combined with C-terminal switches.

It appears that the cysteine residues at position 9 and 10 of $\alpha_q$ can affect both receptor and effector interaction. In particular, it has been reported that the loss of both cysteine residues resulted in the impairment of both receptor interaction and effector function (see, e.g., J. R. Hepler et al., J. Biol. Chem., 271: 496–504, 1996; and M. D. Edgerton et al., FEBS Letters 354: 195–199, 1994). In our presently preferred examples, at least one of these cysteine residues is retained in the $\alpha_q$ mutants. However, Gi-type G proteins are generally myristoylated at their amino termini (id.), which can be useful in connection with the $\alpha_q$ mutans of the present invention, particularly where increasing cross-talk with the Gi-type GPCRs is desired.

In a first exemplary embodiment, a nucleic acid of an $\alpha_q$ mutant encodes a truncated protein lacking the first six N-terminal amino acids (hereafter referred to as the "–6q" mutant) (see Example 1 and FIG. 2A). We have found that such truncation at the N-terminus confers receptor coupling promiscuity to the G protein, which apparently results from an acquired ability to respond to Gi-type and Gs-type GPCRs. Such altered G proteins can be recognized and activated by, for example, GPCRs of the Gi/o family (such as m2 muscarinic receptors and D2 dopamine receptors), and GPCRs of the Gs family (such as D1 dopamine receptors, V2 vasopressin receptors and β2-adrenergic receptors), as described below.

Another exemplary embodiment of this invention provides nucleic acids encoding chimeric $\alpha_q$ subunits, in which the N-terminal sequences are replaced with corresponding sequences from non-q-type G proteins (such as Gi-type or Gs-type proteins). The new N-terminal domain derived from other families of $G_\alpha$ subunits allows the mutant to associate with certain GPCRs in addition to $G_q$-type GPCRs, while nevertheless retaining the ability to engage in q-type downstream signaling (e.g. through the PLC pathway). An exemplary nucleic acid encodes a chimeric $\alpha_q$ mutant whose first N-terminal six amino acids are removed, and the next four residues are replaced with the corresponding $a_i$ residues (hereafter referred to as "i4q"). Alteration of the N-terminal 10 amino acids allowed coupling to $G_i$-coupled m2 muscarinic receptor which normally does not interact with $G_q$. For instance, in the presence of i4q, the m2 muscarinic receptor exhibited the ability to productively couple to $\alpha_q$ as indicated by an increase in inositol phosphate level.

N-terminal mutations can also be made in combination with C-terminal alterations such as those previously described by Conklin et al. (see B. R. Conklin et al., Nature 363: 274–276, 1993; and B. R. Conklin et al., Molecular Pharmacology 50: 885–890, 1996). In the first report (Nature 1993), C-terminal chimeras were generated by replacing C-terminal amino acids of $\alpha_q$ with the corresponding residues of $\alpha_{i2}$ to create $\alpha_q/\alpha_i$ chimeras that can mediate stimulation of phospholipase C by receptors otherwise coupled exclusively to $G_i$. A minimum of four $\alpha_{i2}$ amino acids from the C-terminus sufficed to switch the receptor of the $\alpha_q/\alpha_{i2}$ chimeras. However, extensive substitutions beyond 10 residues from the C-terminus reduced the ability of the chimeras to mediate a productive coupling with $G_i$-linked receptors, possibly due to disruption of the tertiary structure of the proteins. Thus, N-terminally altered proteins as described herein can be further modified at the C-terminus according to the scheme outlined by Conklin et al. to generate a host of double mutants (also referred to as "double chimeras"). As described below, such double chimeras exhibit significant improvement relative to the C-terminal chimeras. Namely, they are better at activating phospholipase C by receptors which have been previously shown to activate the C-terminal chimeras, and by additional receptors that the C-terminal chimeras apparently did not recognize.

An exemplary double chimera of the $\alpha_q$ subunit (hereafter referred to as "i4qi4") has the first six residues removed, the next four N-terminal residues changed to $G_{\alpha i}$ (as in i4q), as well as four residues at the C-terminus changed to $G_{\alpha i}$ residues. In the presence of i4qi4, m2 muscarinic receptor can activate PLCs to a greater extend. In addition, the somatostatin 1 receptor, which did not interact with C-terminal chimeras, did recognize i4qi4 and mediated a strong PLC response.

The subsequent report by Conklin et al. (in Molecular Pharmacology 50: 885–890, 1996) demonstrated switching based on C-terminal alterations from $\alpha_q$ to $\alpha_s$, which can also be employed in the context of the present invention.

Nucleic acids encoding G proteins and GPCRs as described herein can be derived from native sources, including both vertebrates and invertebrates, plants or fungi. Preferably, the nucleic acid is from vertebrates, most preferably from a mammal.

The invention also encompasses nucleic acids encoding for functionally equivalent variants and derivatives of $\alpha_q$ mutants. For instance, changes in a DNA sequence that do not change the encoded amino acid sequence, as well as those that result in conservative substitutions of amino acid residues, and substitution of amino acid residues by amino acid analogs are those which will not significantly affect properties of the encoded polypeptide. Nucleotide substitutions that do not alter the amino acid residues encoded can be useful for optimizing gene expression in different systems.

Uses of nucleic acids encoding $\alpha_q$ mutants include one or more of the following: producing mutated $\alpha$ subunits which can he used, for example, for structure determination, to assay a molecule's activity on a GPCRs, and to screen for molecules useful as diagnostics and/or therapeutics. The $\alpha_q$ mutant can also be expressed as a fusion protein in order to facilitate its purification and/or identification.

As discussed herein, presently preferred G protein mutants comprise promiscuous $G\alpha_q$ mutants having N-terminal and/or C-terminal alterations that mediate shunting of non-q-type upstream signaling events to q-type downstream effectors that can be readily assayed using high throughput screening techniques. However, analogous techniques can be used to generate promiscuous mutants of other G protein $\alpha$ subunits. For example, a screening technique applicable for assaying $G_{12}$-type effector activity could be applied to the screening for modulators of non-$G_{12}$-type GPCRs (such as Gs-, Gi- or Gq-type GPCRs) by switching the corresponding N-terminal and/or C-terminal residues of the $G\alpha_{12}$ subunit to one of these other receptor types using means analogous to those described herein.

Preparation of Nucleic Acids Encoding $\alpha_q$ Mutants

The nucleic acids of this invention can be readily obtained using chemical synthesis, recombinant methods, or PCR.

Methods of chemical polynucleotide synthesis are well known in the art. For example, one of skill in the art can use the sequence information provided herein and in gene banks such as GenBank and a commercial DNA synthesizer to produce a desired DNA sequence.

For preparing $\alpha_q$ mutant polynucleotides using recombinant methods, a polynucleotide comprising a desired sequence can be inserted into a suitable vector, and the vector in turn can be introduced into a suitable host cell for replication and amplification (see Example 1). Polynucleotides can be inserted into host cells by any means known in the art. By way of illustration, cells are transformed by introducing an exogenous polynucleotide by direct uptake, endocytosis, transfection, or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art; see, e.g., *PCR: The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989).

Vectors Containing Nucleic Acids Encoding $\alpha_q$ Mutants

The present invention further includes a variety of vectors (i.e., cloning and expression vectors) having cloned therein $\alpha_q$ mutant polynucleotide(s). These vectors can be used for expression of recombinant polypeptides as well as a source of $\alpha_q$ mutant polynucleotides. Cloning vectors can be used to obtain replicate copies of the $\alpha_q$ mutant polynucleotides they contain, or as a means of storing the polynucleotides for future use. Expression vectors (and host cells containing these expression vectors) can be used to obtain polypeptides produced from the polynucleotides they contain.

Cloning and expression vectors generally contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selectable marker genes encode protein (s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of a suitable marker gene will depend on the host cell, and appropriate genes for different hosts are known in the art. Cloning and expression vectors also typically contain a replication system recognized by the host.

Suitable cloning vectors can be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen. The Examples provided herein also provide examples of cloning vectors.

Expression vectors generally are replicable polynucleotide constructs that contain a polynucleotide encoding an $\alpha_q$ mutant polypeptide of interest. The polynucleotide encoding the $\alpha_q$ mutant polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from $\alpha_q$ polynucleotides (i.e., the $\alpha_q$ gene), or they may be heterologous (i.e., derived from other genes and/or other organisms). A polynucleotide sequence encoding a signal peptide can also be included to allow an $\alpha_q$ mutant polypeptide to lodge in cell membranes (or to be secreted from the cell as a means of facilitating protein purification). A number of expression vectors suitable for expression in eukaryotic cells including yeast, avian, and mammalian cells are known in the art. The Examples provided herein contain examples of expression vectors for mammalian systems.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or $\alpha_q$ mutant polynucleotides will often depend on the host cell.

Host Cells Transformed with $\alpha_q$ Mutant Polynucleotides

Another embodiment of this invention provides host cells transformed with vectors having $\alpha_q$ mutant polynucleotide (s) sequences, as described above. For protein expression, eukaryotic host cells should be used. Among eukaryotic hosts are yeast, insect, avian, plant and mammalian cells, as are known in the art.

The host cells of this invention can be used, inter alia, as repositories of $\alpha_q$ mutant polynucleotides and/or vehicles for production of $\alpha_q$ mutant polynucleotides and/or polypeptides. In certain embodiments, host cells expressing $\alpha_q$ mutants are used in screening methods, described in detail below.

Screening Procedures for Identifying Agents which Modulate GPCR Activities Using $\alpha_q$ Mutants Compounds targeted to GPCRs have several uses including diagnostic uses and therapeutic uses. In one embodiment, G$\alpha_q$ mutants of the present invention can be used for identifying or characterizing agents that modulate the activities of non-G$_q$-interactive receptors. These agents include agonists and antagonists of GPCRs (sometimes collectively referred to as ligands) as well as agents capable of modulating interactions between the receptors and heterotrimeric G proteins.

While crude receptor signaling studies can be performed outside of cells using, for example, reconstituted vesicles (see, e.g., J. R. Hepler, J. Biol. Chem. 271: 496–504, 1996), it is preferable to employ cell-based functional assays.

A preferred method for identifying GPCR modulators in a tested sample generally includes the following steps: (a) providing a host cell expressing, or preferably overexpressing, a GPCR of interest and an altered Gq protein according to the present invention, (b) exposing the cell to a test sample containing a candidate GPCR modulator, and (c) detecting a q-type G protein response within the host cell. Suitable conditions to allow binding of agent to a receptor are physiological conditions wherein the pH is maintained between 6 and 8, and the temperature is between about 20–40 degrees C. As used herein, the binding of ligand to a receptor is understood to denote an interaction of a molecule with the ligand-binding domain of a receptor, which may result in a conformational change in topology of the receptor. The binding of ligand to a receptor may either trigger (in the case of agonist) or block (in the case of antagonist) a detectable intracellular response that is normally associated with signal transduction via q-type G proteins. Such q-type intracellular responses for use in the present invention include (1) activation of phospholipase C proteins; (2) increase in phosphatidylinositol (PI) hydrolysis; (3) and increase in intracellular calcium. Antagonists can be detected by their ability to prevent or limit these responses in cells that have been treated with a known agonist. A signaling modulator may also be identified by its ability to alter the interaction between the receptor and heterotrimeric G protein.

Methods of measuring intracellular inositol phosphates are well known in the art and are exemplified in Example 3. Briefly, cell membrane phospholipids can be labeled by incubating host cells with [$^3$H]myo-inositol for 20–24 hours. Cells are then stimulated with appropriate agonist. Cell extracts can be collected and inositol phosphates separated by ion-exchange chromatography (e.g., by using AG1-X8 in either the chloride- or formate-form; when only IP$_3$ levels are to be determined, the chloride-form is preferably used, whereas the formate form can be used to resolve the major inositol phosphates (IP$_3$, IP$_2$ and IP$_1$)).

Measuring intracellular calcium fluctuation can be rapidly accomplished with the use of calcium-sensitive fluorescent probes, including but not limited to Fura-2, Fluo-3 and Calcium Green-1. Changes of calcium level are reflected by a change in fluorescence of these probes, which can be measured by a high throughput assay that is adaptable to robotic processing. For example, host cells loaded with fluorescent probes can be monitored by FLIPR (Molecular Devices Corp.), an instrument capable of performing stimulation in all 96 wells of samples contained in a microplate simultaneously, and providing real-time measurement and functional data once every second. Typically, the assay is completed in less than fifteen minutes. Since more than a hundred 96-microplates can be read in a day, nearly 10,000 different compounds can be tested for GPCR agonist or antagonist activities by using the mutants of the present invention to shift non-q-type signaling to q-type signaling which can be measured in high throughput assays. A variety of cell types, both adherent and non-adherent, can be used in FLIPR.

Another exemplary high throughput calcium assay involves induction of a reporter gene operatively linked to a calcium-responsive promoter. In this method, a calcium flux resulting from the activation of GPCR turns on the promoter which subsequently drives the expression of a reporter gene encoding a protein with an enzymatic activity that can be easily detected, preferably by a colorimetric or fluorescent assay. Commonly used reporter proteins include: β-galactosidase, β-lactamase, chloramphenicol acetyltransferase (CAT), luciferase, green fluorescent protein (GFP) and its derivatives, among others. Reporter proteins can also be linked to other proteins whose expression is dependent upon the stimulation of GPCRs. An illustrative example would be a fusion protein comprising luciferase sequence in frame with the open-reading frame of nuclear factor of activated T cells (NFAT). Since the transcription of NFAT requires the co-activation of calcium and protein kinases C signaling pathways acting downstream of GPCRs, an effective coupling of heterotrimeric G protein to the receptors can then be measured by assaying NFAT-mediated luciferase activity. This system has been employed to demonstrate a carbachol dependent luciferase response in cells co-expressing muscarinic m3 receptor and chimeric $\alpha_q$ mutant i5q (Boss et al., J. Biol. Chem., 271: 10429–10482, 1996). In practice of this method, a preferred host cell is one of lymphoid or neuronal origin, such as Jurkat cells and pheochromocytoma PC12 cells. However, the choice of host cells is not limited to these two types, as NFAT and NFAT isoforms are present in a variety of cells including endothelial and myeloid cells (id).

In a preferred embodiment, the method of screening agents acting on GPCR signal pathways involves host cells co-expressing the GPCR of interest and suitable $G\alpha_q$ mutant so as to enhance the signal. Even more preferably, expression of GPCRs or $G\alpha_q$ mutant is controlled by an inducible promoter, numerous examples of which have been described in the art and are generally available. If an agent elicits or alters an intracellular response characteristic of $G_q$-coupled receptor in a cell in which the inducible promoter is activated, an observation that the agent fails to elicit the same result in a cell in which the inducible promoter is not activated provides confirmation that the agent is affecting at least one step or aspect of GPCR function. Conversely, if the response is also observed in a cell in which the inducible promoter is not activated, then it can be assumed that the agent is not necessarily acting solely via the GPCR signal transduction pathway.

The invention also encompasses therapeutic agents identified by the method provided by the invention. Active agents may be selected from large collections or libraries of molecules (e.g. combinatorial libraries, proprietary compound libraries held by large drug companies, etc.). A vast array of compounds can be synthesized via biological or biochemical means. The selected agent can be a biological or chemical compound such as a simple or complex organic or inorganic molecule, a peptide, a protein or an oligonucleotide or oligopeptides. In addition, various natural sources can provide compounds for screening, such as plant or animal extracts, and the like.

In another embodiment of the invention, $\alpha_q$ mutants can be used for detailed structure-function studies of mutant receptors using the same procedures mentioned above for identifying agents active at GPCRs.

The following Examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLE 1
Generation of a First N-terminally Altered Gα Mutant

As a first example of a mutant $G\alpha_q$ subunit having an alteration affecting the N terminus, we constructed an $\alpha_q$ subunit (called "-6q") missing the first six amino acids.

To create a construct coding for a mutant $G\alpha_q$ subunit lacking the first six amino acids (-6q), a pcDNAI-based expression plasmid coding for murine WTq, (Strathmann, M. et al. (1990) Proc. Natl. Acad. Sci. 87:9113–9117, Wedegaertner, P. B. et al. (1993) J. Biol. Chem. 268:25001–25008) was used. To generate the -6q expression plasmid, a 78 base-pair synthetic BamHI-FspI fragment containing the desired deletion was used to replace the corresponding sequence in the wild type plasmid. In both plasmids (WTq and -6q), the BamHI site of the pcDNAI polylinker was immediately followed by the initiating ATG codon. Both plasmids contained a short sequence coding for an internal hemagglutinin (HA) epitope tag (DVPDYA) which replaced WTq residues 125–130 (Wedegaertner, P. B. et al. (1993) J. Biol. Chem. 268:25001–25008). The presence of the epitope tag did not affect the receptor and effector coupling properties of WTq (Conklin, B. R. et al. (1993) Nature 363:274–276, Liu, J. et al. (1995) Proc. Natl. Acad. Sci. U.S.A. 92:11642–11646, Wedegaertner, P. B. et al. (1993) J. Biol. Chem. 268:25001–25008). The identity of the two G protein constructs was verified by dideoxy sequencing (Sanger, F. et al. (1977) Proc. Natl. Acad. Sci. U.S.A. 74:5463–5467).

The -6q mutant was employed in various signal transduction studies as described below.

EXAMPLE 2
Expression of Receptor and $G\alpha_q$ Mutant Constructs in Mammalian Host Cells This example illustrates the introduction and expression of G-protein-coupled receptor constructs and mutant G proteins in mammalian host cells suitable for the analysis of G protein-mediated signal transduction.

COS-7 cells were grown in Dulbecco's modified Eagle's medium, supplemented with 10% fetal calf serum, at 37° C. in a humidified 5% $CO_2$ incubator. For transfections, $1\times10^6$ cells were seeded into 100-mm dishes. About 24 h later, COS-7 cells were co-transfected with expression plasmids coding for WTq or -6q (1 mg DNA/dish) and the indicated receptor cDNAs (4 mg DNA/dish), by using a DEAE/dextran procedure (Cullen, B. R. Methods Enzymol. (1987) 152:684–704).

The following receptor expression plasmids were used: m2 muscarinic receptor in pcD (Bonner, T. I. et al. (1987) Science 237:527–532), D2 dopamine receptor (Grandy, D. K. et al. (1989) Proc. Natl. Acad. Sci. U.S.A. 86:9762–9766) in pcDNAI, k-opioid receptor (Zhu, J. et al. (1995) Life Sci. 56:201–207) in pcDNA3, somatostatin SSTR1 receptor (Yamada, Y. et al. (1992) Proc. Natl. Acad. Sci. U.S.A. 89:251–255) in pCMV, A1 adenosine receptor (Mahan, L. C. et al. (1991) Mol. Pharmacol. 40:1–7) in CDM7, D1 dopamine receptor (Zhou, Q. Y. et al. (1990) Nature 347:76–80) in pcDNAI, V2 vasopressin receptor in pcD-PS (Schöneberg, T. et al. (1996) EMBO J. 15:1283–1291), and β2-adrenergic receptor (Gocayne, J. et al. (1987) Proc. Natl. Acad. Sci. USA 84:82968300) in pSVL.

Signal transduction (in response to GPCR agonists) in the transformed cells was analyzed as described below.

EXAMPLE 3
PI Hydrolysis Assay in Transformed Cells

Approximately 24 h after transfections, cells were split into six-well dishes (ca. $0.4\times10^6$ cells/well) in culture medium supplemented with 3 $\mu$Ci/ml [$^3$H]myo-inositol (20 Ci/mmol; American Radiolabeled Chemicals Inc.). After a 24-h labelling period, cells were preincubated for 20 min at room temperature with 2 ml Hank's balanced salt solution containing 20 mM HEPES and 10 mM LiCl. Cells were then stimulated, in the same buffer, with the appropriate agonist ligands (1 h at 37° C.), and increases in intracellular inositol monophosphate ($IP_1$) levels were determined by anion exchange chromatography as described (Kostenis, E. et al. (1997) *Biochemistry* 36:1487–1495).

In a subset of experiments, transfected cells were incubated with pertussis toxin (pertussis toxin 500 ng/ml) for the last 18–24 h of culture.

EXAMPLE 4

Receptor Coupling Properties of Wild-type q (WTq) and -6q

Figure 3:
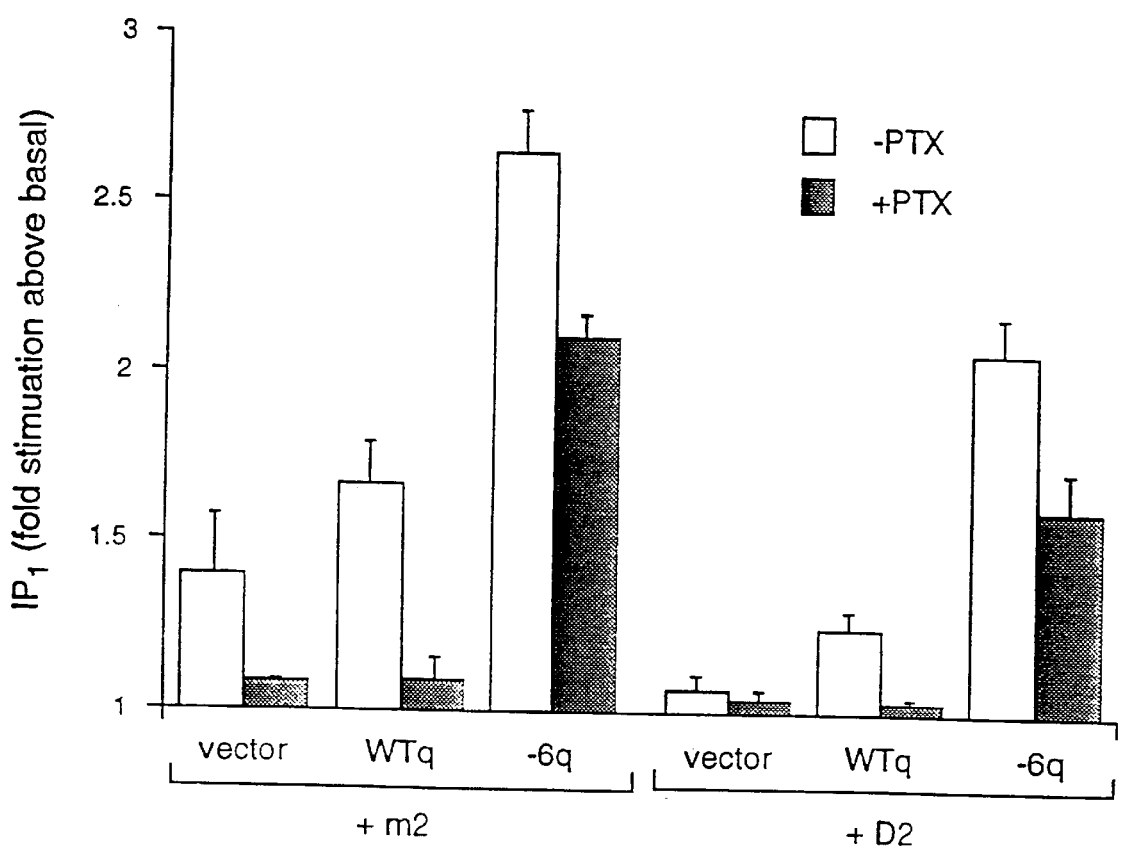
FIG. 3 depicts the effect of pertussis toxin on inositol phosphate accumulation in cells co-transfected with WTq or −6q and Gi/o-coupled receptors. COS-7 cells were co-transfected with expression plasmids coding for the wild type m2 or the D2 dopamine receptor and vector DNA (pcDNAI), WTq, or −6q. Transfected cells were incubated for 1 h (at 37° C.) in the absence or presence of the appropriate agonist ligands. The resulting increases in intracellular $IP_1$ levels either in the absence or in the presence of PTX (500 ng/ml). Data are given as means ±S.E. of four independent experiments, each carried out in triplicate. The following ligands were used: m2 muscarinic receptor, carbachol (100 μM); D2 dopamine receptor, (−)-quinpirole (10 μM).

A series of receptors that are preferentially coupled to G proteins of the Gi/o family (m2 muscarinic, D2 dopamine, κ-opioid, SSTR1 somatostatin, and A1 adenosine) were co-expressed in COS-7 cells with either WTq or -6q. Transfected cells were then incubated with the appropriate agonist ligands, and the ability of the different receptors to couple to the two G proteins was determined by measuring increases in inositol phosphate production (due to WTq-mediated activation of PLCβ; Smrcka, A. V. et al. (1991) *Science* 251:804–807; Berstein, G. et al. (1992) *J. Biol. Chem.* 267:8081–8088). Co-expression of the different Gi/o-coupled receptors with either vector DNA (pcDNAI) or WTq, followed by ligand stimulation, resulted only in a rather small increase in PLCβ activity (FIG. 2A). As shown in FIG. 3 for the m2 muscarinic and D2 dopamine receptors, this small increase in inositol phosphate production could be almost completely blocked by pretreatment of cells with pertussis toxin (500 ng/ml). Consistent with previous findings (Ashkenazi, A. et al. (1987) *Science* 238:672–675, Offermanns, S. et al. (1994) *Mol. Pharmacol.* 45:890–898), this observation suggests that the m2 muscarinic and D2 dopamine receptors do not couple to WTq to a significant extent and that the small increase in PI hydrolysis seen after stimulation of these receptors is most likely due to activation of PLCβ by G protein βγ subunits released upon receptor-mediated activation of endogenous Gi/o proteins (Katz, A. et al. (1992) *Nature* 360:686–689, Camps, M. et al.(1992) *Nature* 360:684–686).

Figure 4A:
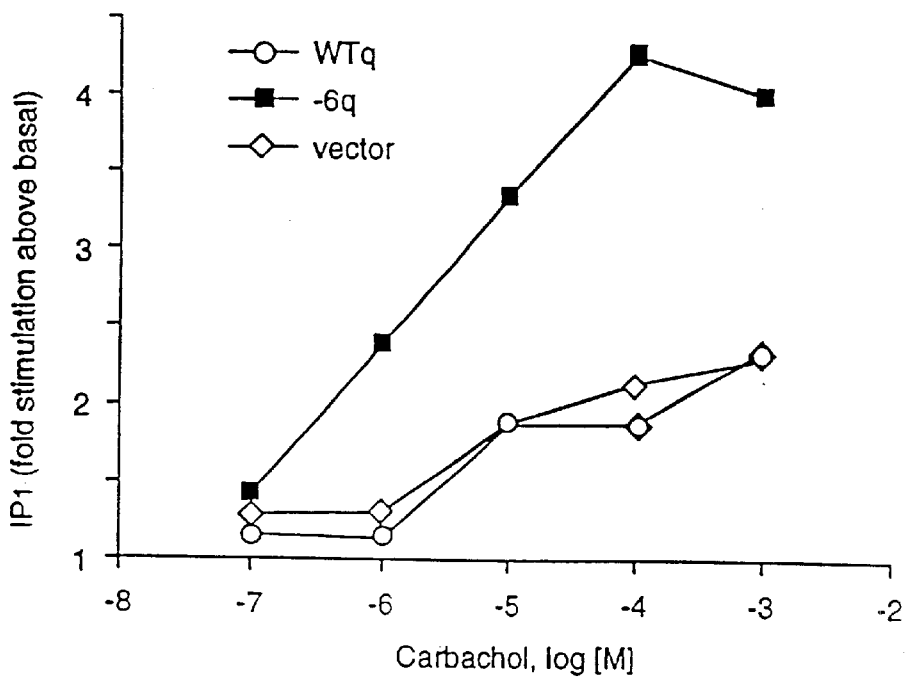
FIG. 4 depicts the functional interaction of the m2 muscarinic and the D2 dopamine receptor with −6q. COS-7 cells co-transfected with vector DNA (pcDNAI), WTq, or −6q and m2 muscarinic (A) or D2 dopamine receptor (B) expression plasmids were incubated for 1 h (at 37° C.) with increasing concentrations of carbachol (A) or (−)-quinpirole (B). The resulting increases in intracellular $IP_1$ levels were determined as described under Example 3. Results (mean values) from a representative experiment, carried out in triplicate, are shown; four additional experiments gave similar results.
Figure 4B:
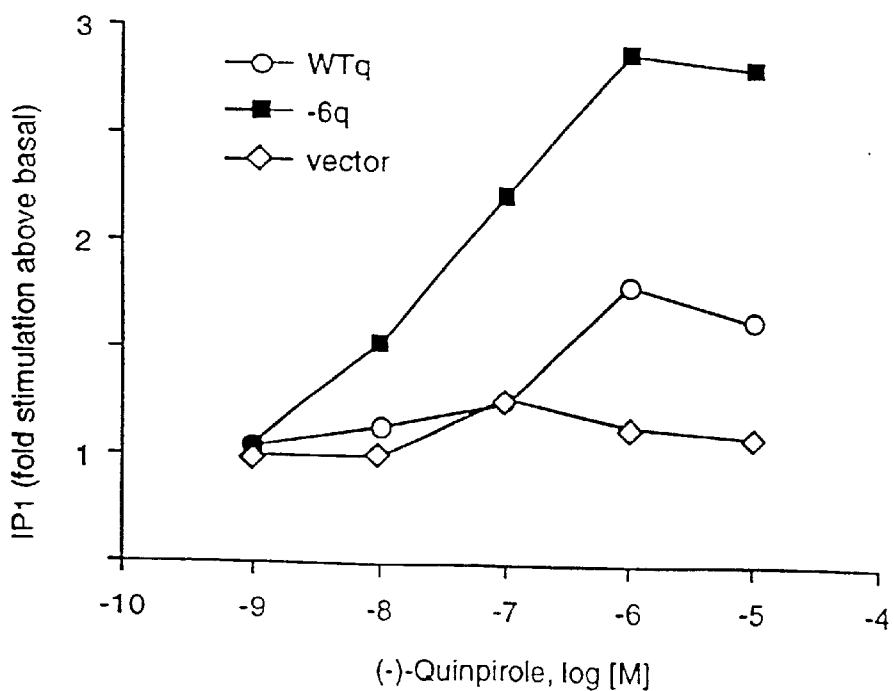

However, co-expression. of the different Gi/o-coupled receptors with -6q resulted in a significantly increased PI response (as compared with WTq) which was most pronounced in the case of the two biogenic amine receptors (m2 muscarinic and D2 dopamine; FIG. 2A). These responses could only be partly blocked by pertussis toxin pretreatment (shown for the m2 muscarinic and D2 dopamine receptors in FIG. 3), indicating that they were primarily due to receptor-mediated generation of activated -6q. Complete concentration-response curves for m2 muscarinic and D2 dopamine receptor-mediated activation of -6q are given in FIG. 4. The EC50 values (means, S.E. of five independent experiments, each carried out in triplicate) for these responses amounted to 7.4±0.3 mM in the case of the muscarinic agonist, carbachol (FIG. 4A), and to 1.4±0.2 mM in the case of the dopaminergic ligand, (-)-quinpirole (FIG. 4B), indicating that the interaction of the two biogenic amine receptors with -6q was highly efficient.

Figure 2B:
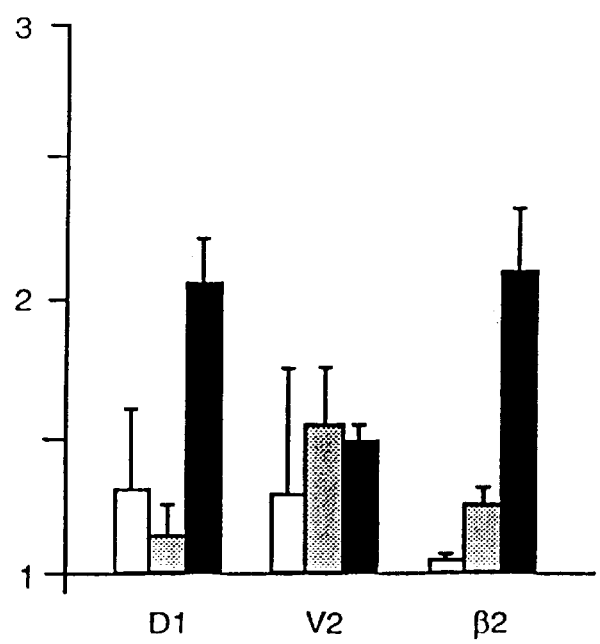

We also examined the ability of three Gs-coupled receptors (D1 dopamine, V2 vasopressin, and β2-adrenergic) to functionally interact with WTq or -6q. Consistent with their known coupling profiles (Watson, S. et al. (1994) in *The G-Protein Linked Receptor—Facts Book* (Watson, S., and Arkinstall, S., eds) pp. 1–291, Academic Press, London), these receptors were unable to activate WTq to an appreciable extent (FIG. 2B). However, two of the investigated $G_s$-coupled receptors (D1 dopamine and β2-adrenergic) gained the ability to induce a significant increase in inositol production when co-expressed with -6q (as compared with WTq; FIG. 2B).

Our data therefore suggest that -6q, in contrast to WTq, can be activated by receptors that are members of all three major functional classes of GPCRs. It should also be noted that co-expressed -6q did not improve coupling of the V2 vasopressin receptor to PLC stimulation and that the absolute magnitude of responses mediated by -6q upon co-expression with the κ-opioid or the SSTR1 somatostatin receptor, respectively, was quite small (FIG. 2), indicating that -6q is not universally promiscuous. One possible reason for the observed differences in the ability of the studied Gi/o- and Gs-coupled receptors to interact with -6q may be that the relative functional importance of individual receptor/G protein contact sites may vary among different GPCRs (e.g. peptide receptors versus receptors for biogenic amines).

EXAMPLE 5

Expression Levels and Subcellular Distribution of $\alpha_q$ Constructs

To exclude the possibility that the promiscuous nature of -6q was simply due to exceptionally high expression levels (as compared to WTq), the subcellular distribution of the two G protein subunits was studied by cell fractionation and immunoblotting.

Cells were fractionated into particulate and soluble fractions as described (Degtyarev, M. Y. et al. (1994) *J. Biol. Chem.* 269:30898–30903). The 12CA5 mouse monoclonal antibody (BAbCo) specific for the HA-epitope was used for immunoprecipitation and immunoblotting. Immunoprecipitation studies were performed using equivalent amounts of protein (2.5 mg) from total cell suspension in solubilization buffer consisting of 50 mM Tris-HCl (pH 7.4), 150 mM NaCl, 1% (w/v) of Nonidet P-40, 0.5% (w/v) sodium deoxycholate, and 0.1% (w/v) SDS in a total volume of 1 ml. Cell suspensions were added to the solubilization buffer and incubated at 4° C. on a rotator for 30 min, followed by centrifugation for 10 min at 14,000 r.p.m. in an Eppendorf 5415 microcentrifuge to pellet insoluble material. Supernatants were transferred to fresh Eppendorf tubes, and 5 mg of 12CA5 antibody and 20 ml of a 50% suspension of Protein A-agarose (Sigma) were added, followed by an overnight incubation at 4° C. on a rotator. Immunoprecipitates were recovered by centrifugation at 1,000×g in a microcentrifuge, washed twice in 1 ml solubilization buffer containing 1/10 of the original detergent concentration, solubilized in 45 ml of gel sample buffer (Novex) in the absence of reducing agents, boiled for 5 min, separated by SDS-PAGE on 10% Tris-Gly gels (Novex), and prepared for fluorography using Amplify (Amersham) according to the manufacturer's instructions.

Fluorograms were exposed for four to six weeks at -70° C. Immunoblotting was performed by separating equal amounts of protein (100 mg) from subcellular fractions solubilized in gel sample buffer (Novex) with 2.5% (v/v) β-mercaptoethanol on 10% Tris-Gly gels (Novex), transfer to nitrocellulose membranes, probing with the 12CA5 antibody conjugated to horse radish peroxidase (Boehringer Mannheim), and development with enhanced chemiluminescence reagents (Amersham). Protein concentrations were determined using the Bio-Rad protein assay kit with IgG as the standard.

Figure 5A:
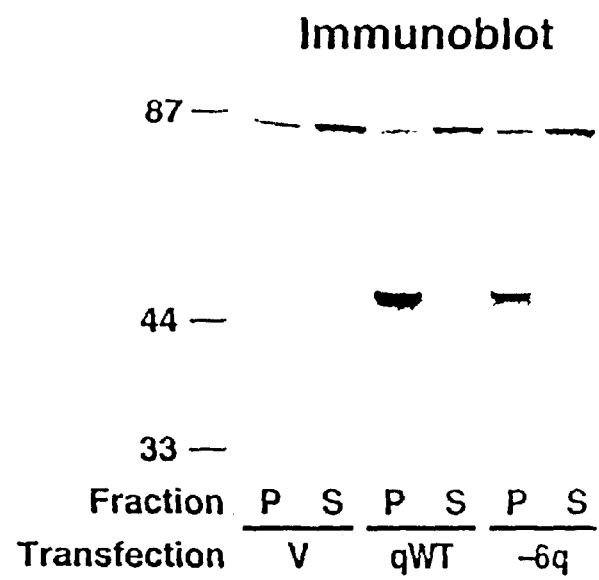
FIG. 5 depicts the subcellular localization and palmitoylation of WTq and −6q. COS-7 cells were transfected with vector DNA alone (V), WTq, or −6q. (A) Cellular proteins were separated into particulate (P) and soluble (S) fractions, and Gα subunits were detected by Western blotting using the HA-epitope specific 12CA5 antibody, as described under "Example 5." (B) Following labeling of cells with [$^3$H] palmitic acid, proteins were immunoprecipitated with the 12CA5 antibody. The immunoprecipitates were resolved by SDS-PAGE and analyzed by fluorography. WTq and −6q proteins run at approximately 44 kDa. Protein molecular weight standards (in kDa) are indicated.

Both Gα subunits were detected with the monoclonal antibody, 12CA5, which recognizes the internal HA-epitope tag present in both proteins (see Example 1). As shown FIG. 5A, both G protein constructs were found exclusively in the particulate fraction; however, -6q was expressed at lower levels (approximately 10–20% of WTq, as determined by scanning densitometry; data not shown). The precise reason for this latter observation remains unclear; however, possible factors may include reduced protein stability or translation efficiency. In any case, these data exclude the possibility that the ability of −6q to be activated by multiple classes of GPCRs is due to overexpression of this subunit (as compared to WTq).

Moreover, they indicate that even relatively reduced levels of a promiscuous Gα mutant can be used to effectively shunt GPCR signal transduction from non-q-type upstream pathways (such as those mediated by Gs-type and Gi-type GPCRs) to q-type downstream pathways (which are readily measurable using high throughput screening techniques).

EXAMPLE 6
Palmitoylation Pattern of WTq and −6q

Previous studies have shown that G proteins of the $G\alpha_q$ family are palmitoylated at cysteine residues located near the N-terminus of the proteins (corresponding to Cys9 and Cys10 in FIG. 1) Edgerton et al. (1994) *FEBS Lett.* 354:195–199; McCallum et al. (1995) *Biochem. J.* 310:1021–1027. To compare the palmitoylation patterns of WTq and −6q, transfected COS-7 cells were metabolically labeled with [$^3$H]palmitic acid, followed by immunoprecipitation of WTq and −6q by the 12CA5 monoclonal antibody, SDS-PAGE, and fluorography.

Figure 5B:
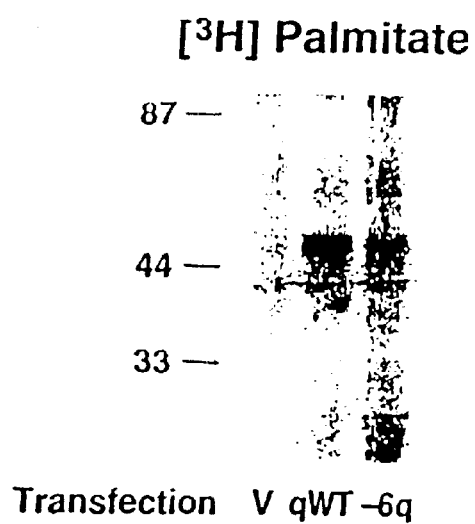

As shown in FIG. 5B, WTq and −6q were the only immunoprecipitated proteins, since no labeled proteins could be precipitated when cells were transfected with "empty" vector DNA. Consistent with published results (Edgerton et al. (1994) *FEBS Lett.* 354:195–199; McCallum et al. (1995) *Biochem. J.* 310:1021–1027), both WTq and −6q (16) incorporated considerable amounts of [$^3$H] palmitate (FIG. 5B). The reduction in signal strength seen with −6q correlated well with the reduction in −6q levels revealed by immunoblotting (FIG. 5A), as discussed above. This observation suggests that −6q is palmitoylated to an extent similar to that of WTq. It is therefore unlikely that differences in palmitoylation patterns are responsible for the different functional properties of −6q and WTq.

EXAMPLE 7
Generation of Additional N-Terminal $G\alpha_q$ Mutants

As an illustrative example of another $G\alpha_q$ mutant, we used techniques analogous to those described above to construct an additional altered $G\alpha_q$ subunit (referred to as "i4q") in which the first six N-terminal residues are deleted, and the next four residues (i.e. residues 7–10) were replaced with residues corresponding to residues 1–4 of a $G_{i\alpha}$ subunit.

Signal transduction studies conducted with this mutant confirmed that it also acquired the ability to shunt non-q-type upstream signaling to q-type downstream effector function.

EXAMPLE 8
Generation of Double $G\alpha_q$ Mutants Having Both N-terminal and C-terminal Alterations As an illustrative example of a double $G\alpha_q$ mutant having both N-terminal and C-terminal alterations, we used techniques analogous to those described above to construct an additional altered $G\alpha_q$ subunit (referred to as "i4qi4") in which the first six N-terminal residues are deleted, and the next four residues (i.e. residues 7–10) were replaced with residues corresponding to residues 1–4 of a $G\alpha_i$ subunit; and the C-terminal region was altered by replacement of the last four amino acids with corresponding residues from the C-terminal region of $G\alpha_i$.

Signal transduction studies conducted with this double mutant confirmed that it also acquired the ability to shunt non-q-type upstream signaling to q-type downstream effector function, and that it appeared to be even more effective at signal transduction than the single N-terminal mutants described above.

What is claimed is:

1. A method for identifying a non-Gq G-protein-coupled receptor (GPCR) modulator, comprising the steps of:
    (i) contacting a candidate non-Gq GPCR modulator with a host cell comprising a non-Gq GPCR and a mutant q-type G protein wherein said mutant comprises an alteration in one or more of the first 10 N-terminal amino acids of the $\alpha_q$ subunit and wherein said mutant is responsive to at least one non-q-type GPCR in said host cell; and
    (ii) assaying for a q-type G protein response.

2. The method according to claim 1, wherein said cell comprises a recombinant polynucleotide encoding a non-q-type GPCR.

3. The method according to claim 1, wherein said cell has been transformed with a vector encoding the mutant q-type protein.

4. The method according to claim 1, wherein assaying for a q-type G protein response comprises assaying for activation of phospholipase C.

5. The method according to claim 1, wherein assaying for a q-type G protein response comprises assaying for hydrolysis of phosphatidylinositols.

6. The method according to claim 1, wherein assaying for a q-type G protein response comprises assaying for calcium mobilization.

7. The method according to claim 1, wherein said modulator is a GPCR agonist that binds to and activates a non-q-type GPCR.

8. A method according to claim 7, wherein said modulator is a GPCR agonist that binds to and activates a Gi-type GPCR.

9. A method according to claim 7, wherein said modulator is a GPCR agonist that binds to and activates a Gs-type GPCR.

10. The method according to claim 1, wherein said modulator is a GPCR antagonist that binds to and competitively inhibits a non-q-type GPCR.

11. The method according to claim 10, wherein said method comprises the additional step of contacting said host cell with an agonist of said non-q-type GPCR.

12. The method according to claim 1, wherein said modulator is a GPCR antagonist that binds to and non-competitively inhibits a non-q-type GPCR.

13. The method according to claim 1, wherein said mutant q-type G-protein transduces the signal of a Gi or Gs type GPCR.

14. The method according to claim 1, wherein said alteration is selected from the group consisting of a deletion, substitution and insertion.

15. The method according to claim 1, wherein said alteration maintains the alpha-helical nature of the N-terminal region.

16. The method according to claim 1, wherein said alteration comprises a substitution of at least one of the first six N-terminal amino acids of the $\alpha_q$ subunit.

17. The method according to claim 1, wherein said alteration comprises a substitution of at least two of the first six N-terminal amino acids of the $\alpha_q$ subunit.

18. The method according to claim 1, wherein said alteration is a deletion of at least one of the first six N-terminal amino acids of the $\alpha_q$ subunit.

19. The method according to claim 1, wherein said alteration is a deletion of at least two of the first six N-terminal amino acids of the $\alpha_q$ subunit.

20. The method according to claim 1, wherein said alteration is a deletion of the first six N-terminal amino acids of the $\alpha_q$ subunit.

21. The method according to claim 1, wherein said mutant further comprises a substitution of at least one of N-terminal amino acids 7–10 of the $\alpha_q$ subunit.

22. The method according to claim 21, wherein said substitution comprises a substitution of at least one of N-terminal amino acids 7, 8, 9 or 10 with an amino acid found at position 1, 2, 3 or 4 of a non-q-type α subunit.

23. The method according to claim 1, wherein said mutant further comprises a C-terminal mutation in which one or more amino acids at the C-terminus of the $\alpha_q$ subunit is replaced with one or more amino acids from the C-terminus of a non-q-type α subunit.

24. A method for identifying a non-Gq G-protein-coupled receptor (GPCR) modulator, comprising the steps of:
   (i) contacting a candidate non-Gq GPCR modulator with a non-Gq GPCR and a mutant q-type G protein wherein said mutant comprises an alteration in one or more of the first 10 N-terminal amino acids of the $\alpha_q$ subunit and wherein said mutant is responsive to said non-q-type GPCR; and
   (ii) assaying for a q-type G protein response.

25. The method according to claim 24, wherein assaying for a q-type G protein response comprises assaying for activation of phospholipase C.

26. The method according to claim 24, wherein assaying for a q-type G protein response comprises assaying for hydrolysis of phosphatidylinositols.

27. The method according to claim 24, wherein assaying for a q-type G protein response comprises assaying for calcium mobilization.

28. The method according to claim 24, wherein said modulator is a GPCR agonist that binds to and activates a non-q-type GPCR.

29. A method according to claim 24, wherein said modulator is a GPCR agonist that binds to and activates a Gi-type GPCR.

30. A method according to claim 24, wherein said modulator is a GPCR agonist that binds to and activates a Gs-type GPCR.

31. The method according to claim 24, wherein said modulator is a GPCR agonist that binds to and competitively inhibits a non-q-type GPCR.

32. The method according to claim 31, wherein said method comprises the additional step of contacting said non-Gq GPCR with an agonist of said non-q-type GPCR.

33. The method according to claim 24, wherein said modulator is a GPCR agonist that binds to and non-competitively inhibits a non-q-type GPCR.

34. The method according to claim 24, wherein said mutant q-type G-protein transduces the signal of a Gi or Gs type GPCR.

35. The method according to claim 24, wherein said alteration is selected from the group consisting of a deletion, substitution and insertion.

36. The method according to claim 24, wherein said alteration maintains the nature of the N-terminal region.

37. The method according to claim 24, wherein said alteration comprises a of at least one of the first six N-terminal amino acids of the $\alpha_q$ subunit.

38. The method according to claim 24, wherein said alteration comprises a substitution of at least two of the first six N-terminal amino acids of the $\alpha_q$ subunit.

39. The method according to claim 24, wherein said alteration is a deletion of at least one of the first six N-terminal amino acids of the $\alpha_q$ subunit.

40. The method according to claim 24, wherein said alteration is a deletion of at least two of the first six N-terminal amino acids of the $\alpha_q$ subunit.

41. The method according to claim 24, wherein said alteration is a deletion of the first six N-terminal amino acids of the $\alpha_q$ subunit.

42. The method according to claim 24, wherein said mutant further comprises a substitution of at least one of N-terminal amino acids 7–10 of the $\alpha_q$ subunit.

43. The method according to claim 42, wherein said substitution comprises a substitution of at least one of N-terminal amino acids 7, 8, 9 or 10 with an amino acid found at position 1, 2, 3 or 4 of a non-q-type α subunit.

44. The method according to claim 24, wherein said mutant further comprises a C-terminal mutation in which one or more amino acids at the C-terminus of the $\alpha_q$ subunit is replaced with one or more amino acids from the C-terminus of a non-q-type α subunit.

45. A recombinant polynucleotide encoding a mutant q-type G protein wherein said mutant comprises a first alteration in one or more of the first 6 N-terminal amino acids of q-type G protein and a substitution of any one of N-terminal amino acids 7–10 of said q-type G protein, wherein said mutant is responsive to at least one non-q-type GPCR.

46. The recombinant polynucleotide according to claim 45, wherein said alteration is selected from the group consisting of a deletion, substitution and insertion.

47. The recombinant polynucleotide according to claim 45, wherein said alteration maintains the alpha-helical nature of the N-terminal region.

48. The recombinant polynucleotide according to claim 45, wherein said first alteration comprises a substitution of at least one of the first six N-terminal amino acids of the $\alpha_q$ subunit.

49. The recombinant polynucleotide according to claim 45, wherein said first alteration comprises a substitution of at least two of the first six N-terminal amino acids of the $\alpha_q$ subunit.

50. The recombinant polynucleotide according to claim 45, wherein said first alteration is a deletion of at least one of the first six N-terminal amino acids of the $\alpha_q$ subunit.

51. The recombinant polynucleotide according to claim 45, wherein said first alteration is a deletion of at least two of the first six N-terminal amino acids of the $\alpha_q$ subunit.

52. The recombinant polynucleotide according to claim 45, wherein said first alteration is a deletion of the first six N-terminal amino acids of the $\alpha_q$ subunit.

53. The recombinant polynucleotide according to claim 45, wherein said substitution of any one of N-terminal amino acids 7–10 comprises a substitution of at least one of amino acids 7–10 of the $\alpha_q$ subunit.

54. The recombinant polynucleotide according to claim 45, wherein said substitution of any one of N-terminal amino acids 7–10 comprises a substitution of at least one of amino acids 7, 8, 9 or 10 with amino acids found at positions 1, 2, 3 or 4 of a non-q-type α subunit.

55. The recombinant polynucleotide according to claim 45, further comprising a C-terminal mutation in which one or more amino acids at the C-terminus of the $\alpha_q$ subunit is replaced with an amino acid from the C-terminus of a non-q-type α subunit.

56. A host cell transformed with a recombinant polynucleotide according to claim 45.

57. The cell of claim 56, further transformed with a recombinant polynucleotide encoding a non-q-type GPCR.

58. The cell of claim 57, wherein said non-q-type GPCR is a Gi-type GPCR.

59. The cell of claim 57, wherein said non-q-type GPCR is a Gs-type GPCR.

60. The recombinant polynucleotide of claim 25 further comprising an additional alteration in the C-terminal region of said q-type G protein, wherein said mutant is responsive to at least one non-q-type GPCR.

61. The recombinant polynucleotide according to claim 60, wherein said mutant further comprises a C-terminal mutation in which one or more amino acids at the C-terminus of the $\alpha_q$ subunit is replaced with one or more amino acids from the C-terminus of a non-q-type $\alpha$ subunit.

62. A recombinant polynucleotide encoding a mutant q-type G protein wherein said mutant comprises a first alteration in one or more of the first 6 N-terminal amino acids of q-type G protein and a second alteration in the C-terminal region of said q-type G protein, wherein said mutant is responsive to at least one non-q-type GPCR.

63. The recombinant polynucleotide according to claim 62, wherein said alteration is selected from the group consisting of a deletion, substitution and insertion.

64. The recombinant polynucleotide according to claim 62, wherein said alteration maintains the alpha-helical nature of the N-terminal region.

65. The recombinant polynucleotide according to claim 62, wherein said first alteration comprises a substitution of at least one of the first six amino acids of the $\alpha_q$ subunit.

66. The recombinant polynucleotide according to claim 62, wherein said first alteration comprises a substitution of at least two of the first six amino acids of the $\alpha_q$ subunit.

67. The recombinant polynucleotide according to claim 62, wherein said first alteration is a deletion of at least one of the first six amino acids of the $\alpha_q$ subunit.

68. The recombinant polynucleotide according to claim 62, wherein said first alteration is a deletion of at least two of the first six N-terminal amino acids of the $\alpha_q$ subunit.

69. The recombinant polynucleotide according to claim 62, wherein said first alteration is a deletion of the first six N-terminal amino acids of the $\alpha_q$ subunit.

70. The recombinant polynucleotide according to claim 62, wherein said mutant further comprises a C-terminal mutation in which one or more amino acids at the C-terminus of the $\alpha_q$ subunit is replaced with one or more amino acids from the C-terminus of a non-q-type $\alpha$ subunit.

71. A host cell transformed with a recombinant polynucleotide according to claim 62.

72. The cell of claim 71, further transformed with a recombinant polynucleotide encoding a non-q-type GPCR.

73. The cell of claim 72, wherein said non-q-type GPCR is a Gi-type GPCR.

74. The cell of claim 72, wherein said non-q-type GPCR is a Gs-type GPCR.

75. A recombinant polynucleotide encoding a mutant q-type G protein wherein said mutant comprises a substitution of at least one of the first six N-terminal amino acids of a q-type G protein, wherein said mutant is responsive to at least one non-q-type GPCR.

76. The recombinant polynucleotide of claim 75 further comprising an additional alteration in the C-terminal region of said q-type G protein, wherein said mutant is responsive to at least one non-q-type GPCR.

77. A recombinant polynucleotide encoding a mutant q-type G protein wherein said mutant comprises a substitution of at least two of the first six N-terminal amino acids of a q-type G protein, wherein said mutant is responsive to at least one non-q-type GPCR.

78. The recombinant polynucleotide of claim 77 further comprising an additional alteration in the C-terminal region of said q-type G protein, wherein said mutant is responsive to at least one non-q-type GPCR.

* * * * *

UNITED STATES PATENT AND TRADEMARK OFFICE
CERTIFICATE OF CORRECTION

PATENT NO.    : 6,383,761 B2
DATED         : May 7, 2002
INVENTOR(S)   : Bruce R. Conklin et al.

It is certified that error appears in the above-identified patent and that said Letters Patent is hereby corrected as shown below:

Column 21,
Line 36, please replace "24" with -- 28 --;
Line 39, please replace "24" with -- 28 --;
Line 49, please replace "agonist" with -- antagonist --;
Line 58, after "alteration maintains the", please insert -- alpha-helical --;
Line 60, after "alteration comprises a", please insert -- substitution --;

Column 23,
Line 3, please replace "25" with -- 45 --.

Signed and Sealed this

Nineteenth Day of November, 2002

*Attest:*

*Attesting Officer*

JAMES E. ROGAN
*Director of the United States Patent and Trademark Office*